United States Patent [19]

Gildemeister et al.

[11] 4,370,320
[45] Jan. 25, 1983

[54] (THIONO) (THIOL) PHOSPHORIC (PHOSPHONIC) ACID ESTERS AND ESTER-AMIDES OF SUBSTITUTED 4-HYDROXYQUINOLINES AND THEIR USE AS AGENTS FOR COMBATING PESTS

[75] Inventors: Horst Gildemeister, Wiesbaden; Hilmar Mildenberger, Kelkheim; Werner Knauf, Frankfurt am Main; Anna Waltersdorfer, Frankfurt am Main; Burkhard Sachse, Kelkheim, all of Fed. Rep. of Germany

[73] Assignee: Hoechst Aktiengesellschaft, Frankfurt am Main, Fed. Rep. of Germany

[21] Appl. No.: 303,475

[22] Filed: Sep. 18, 1981

[30] Foreign Application Priority Data

Sep. 20, 1980 [DE] Fed. Rep. of Germany ....... 3035650

[51] Int. Cl.³ ................. A61K 31/675; C07D 215/56
[52] U.S. Cl. ..................................... 424/200; 546/23
[58] Field of Search ........................... 546/23; 424/200

[56] References Cited

U.S. PATENT DOCUMENTS 3,042,703 7/1962 Schegh et al. ..................... 260/973
3,892,753 7/1975 Fest et al. .............................. 546/23

OTHER PUBLICATIONS

Kosolapoff, Organophosphorous Compounds, (1950), John Wiley, pp. 224–225.

Primary Examiner—Henry R. Jiles
Assistant Examiner—Bernard Dentz
Attorney, Agent, or Firm—Curtis, Morris & Safford

[57] ABSTRACT

Phosphoric and phosphonic acid derivatives of substituted 4-hydroxyquinolines of the formula

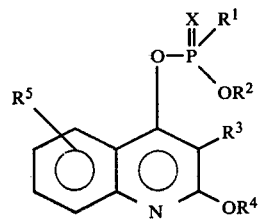

in which $R^1$ denotes alkyl, alkoxy, alkylthio, (di)alkylamino or phenyl, $R^2$ and $R^4$ denote alkyl, $R^3$ denotes H, halogen, carbalkoxy, substituted carbonamido or CN, $R^5$ denotes H, halogen, $NO_2$, alkyl, alkoxy or $CF_3$ and X denotes O or S, are effective insecticides and fungicides.

6 Claims, No Drawings

(THIONO) (THIOL) PHOSPHORIC (PHOSPHONIC) ACID ESTERS AND ESTER-AMIDES OF SUBSTITUTED 4-HYDROXYQUINOLINES AND THEIR USE AS AGENTS FOR COMBATING PESTS

The invention relates to compounds of the formula I

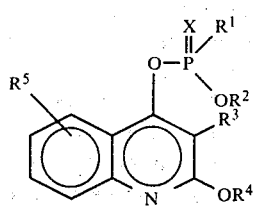

in which $R^1$ denotes $(C_1-C_4)$-alkyl, $(C_1-C_4)$-alkoxy, $(C_1-C_4)$-alkylthio, $(C_1-C_4)$-alkylamino, $(C_1-C_4)$-dialkylamino or phenyl, $R^2$ denotes $(C_1-C_4)$-alkyl, $R^3$ denotes hydrogen, halogen, COOalkyl, CONH(alkyl) or CON(alkyl)$_2$ with in each case 1-4 C atoms per alkyl radical, or CN, $R^4$ denotes $(C_1-C_4)$-alkyl, $R^5$ denotes hydrogen, halogen, nitro, $(C_1-C_4)$-alkyl, $(C_1-C_4)$-alkoxy or trihalogenomethyl and X denotes oxygen or sulfur.

Here and in the text which follows, "halogen" preferably denotes fluorine, chlorine or bromine, in particular chlorine.

The invention also relates to a process for the preparation of compounds of the formula I, which comprises reacting 4-hydroxyquinolines of the general formula II

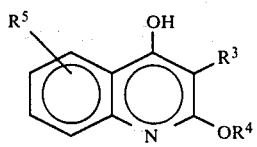

in which $R^3$, $R^4$ and $R^5$ have the meanings given under the general formula I, with (thiono) (thiol) phosphoric (phosphonic) acid ester chlorides or ester-amide chlorides of the general formula III

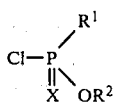

in which $R^1$, $R^2$ and X have the meanings given under the general formula I, in the presence of acid-binding agents.

The reactions are advantageously carried out in a solvent which is inert under the reaction conditions, such as, for example, a lower ketone, acetonitrile, dimethylformamide, dimethylsulfoxide, glycoldimethylether, diisopropylether, benzene, toluene, xylene, chlorobenzene, ethyl acetate or dichloroethane, at temperatures between room temperature and the boiling point of the solvent used, preferably at 40°-90° C. It is necessary to add an acid-binding agent in order to bind the hydrogen chloride liberated. Acid-binding agents which can advantageously be used are alkali alcoholates or carbonates or organic bases, such as pyridine or triethylamine. The 4-hydroxyquinolines of the general formula II used as the starting material have already been described in some cases, or they can be prepared by methods which are known from the literature [for example J. Y. Merour et al, Synthesis 1978, pages 698–700]. The (thiono) (thiol) phosphoric (phosphonic) acid ester chlorides and esteramide chlorides of the general formula III employed are known and can be prepared by customary processes [Houben-Weyl, Vol. XII/1, page 560; Vol. XII/2, pages 274, 607, 621, 755; and Soviet Union Patent Specification No. 184,863].

The compounds of the formula I are distinguished by a good acaricidal and insecticidal activity. The latter is directed both towards sucking and towards biting insects.

The sucking insects which can be combated with the compounds according to the invention include, for example, aphids (Aphididae), such as the green peach aphid (*Myzus persicae*) and the black bean aphid (*Doralis fabae*), courpea aphid (*Aphis craccivora*), the bird cherry aphid (*Rhopalosiphum padi*), the pea aphid (*Macrosiphum pisi*) and the potato aphid (*Macrosiphum solanifolii*), as well as the current gall aphid (*Cryptomyzus korschelti*), the rosy apple aphid (*Sappaphis mali*), the mealy plum aphid (*Hyalopterus arundinis*) and the cherry black-fly (*Myzus cerasi*); thrips (Thysanoptera), such as *Hercinothrips femoralis*, and bugs, for example the beet bug (*Piesma quadrata*), the red cotton bug (*Dysdercus intermedius, Oncopeltus fasciatus*), the bed bug (*Cimex lectularius*), the assassin bug (*Rhodnius prolixus*) and Chagas' bug (*Triatoma infestans*) and furthermore cicadas, such as *Euscelis bilobatus* and *Nephotettix bipunctatus*.

The following biting insects should be mentioned: butterfly caterpillars (Lepidoptera) such as the diamond-back moth (*Plutella maculipennis*), the gipsy moth (*Lymantria dispar*), the brown-tail moth (*Euproctis chrysorrhoea*) and the tent caterpillar (*Malacosoma neustria*), and also the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), and the ermine moth (*Hyponomeuta padella*), the Mediterranean flour moth (*Ephestia k/ hniella*) and the greater wax moth (*Galleria mellonella*).

The biting insects also include beetles (Coleoptera), for example the granary weevil (*Calandra granaria*), the Colorado beetle (*Leptinotarsa decemlineata*), the blossom beetle (*Meligethes aeneus*), the raspberry beetle (*Byturus tomentosus*), the bean weevil (*Acanthoscelides obtectus*), the leather beetle (*Dermestes frischi*), the khapra beetle (*Trogoderma granarium*), the flour beetle (*Tribolium castaneum*), the northern corn billbug (*Sitophilus zeamais*), the drugstore beetle (*Stegobium paniceum*), the yellow mealworm (*Tenebrio molitor*) and the saw-toothed grain beetle (*Oryzaephilus surinamensis*); cockroaches, such as the German cockroach (*Blatella germanica*), the American cockroach (*Periplaneta americana*), the Madeira cockroach (*Leucophaea maderae*), the oriental cockroach (*Blatta orientalis*), the giant cockroach (*Blaberus giganteus*) and the black giant cockroach (*Blaberus fuscus*); and also Orthoptera, for example the house cricket (*Acheta domesticus*).

The Diptera comprise essentially flies, such as the vinegar fly (*Drosophila melanogaster*), the Mediterranean fruit fly (*Ceratitis capitata*), the house fly (*Musca domestica*), the little house fly (*Fannia canicularis*), the black blow-fly (*Phormia aegina*) and the bluebottle fly (*Calliphora erythrocephala*) as well as the stable fly (*Stomoxys calcitrans*); and also gnats, for example mosquitoes, such as the yellow fever mosquito (*Aedes aegypti*), the northern house mosquito (*Culex pipiens*) and the malaria mosquito (*Anopheles stephensi*).

The mites (Acari) include, in particular, the spider mites (Tetranychidae) such as the two-spotted spider mite (*Tetranychus urticae*) and the European red mite (*Panonychus ulmi*), gall mites, for example the blackcurrant gall mite (*Eriophyes ribis*), and tarsonemids, for example the broad mite (*Hemitarsonemus latus*) and the cyclamen mite (*Tarsonemus pallidus*).

When used against hygiene pests and pests of stored products, in particular flies and gnats, the process products also exhibit an outstanding residual action on wood and clay.

Moreover, the compounds claimed have a very good fungicidal, and in some cases systemic, action against phytopathogenic fungi and are therefore outstandingly suitable as plant protection agents. The compounds prevent, for example, *Phytophthora infestans, Plasmopara viticola, Pythium ultimum, Venturia inaequalis, Rhizoctonia solani* and powdery mildew fungi. They have an excellent fungicidal action against *Piricularia oryzae* and various rust fungi.

The invention thus also relates the acaricidal, insecticidal and fungicidal agents, which, in addition to the customary formulation auxiliaries and inert substances, contain compounds of the formula I, and to the use of the compounds for combating acaridae, insects and phytopathogenic fungi.

The agents according to the invention generally contain the active compounds of the formula I in amounts of 1–95% by weight. They can be used as wettable powders, emulsifiable concentrates, solutions which can be sprayed, dusting agents or granules, in the customary formulations.

Wettable powders are products which can be uniformly dispersed in water and which, in addition to the active compound and as well as a diluent or inert substance, also contain wetting agents, for example polyoxyethylated alkyl phenols, polyoxyethylated fatty alcohols and alkyl- or alkylphenyl-sulfonates, and dispersing agents, for example sodium lignin-sulfonate, sodium 2,2'-dinaphthylmethane-6,6'-disulfonate, sodium dibutylnapthalenesulfonate, or sodium oleyl-methyl-taurate.

Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Examples of emulsifiers which can be used are: calcium alkylarylsulfonates, such as Cadodecylbenzenesulfonate, or non-ionic emulsifiers, such as fatty acid polyglycol esters, alkylarylpolyglycol ethers, fatty alcohol polyglycol ethers, propylene oxide/ethylene oxide condensation products, fatty alcohol/propylene oxide/ethylene oxide condensation products, alkyl polyethers, sorbitane fatty acid esters, polyoxyethylene sorbitane fatty acid esters or polyoxyethylene sorbital esters.

Dusting agents are obtained by grinding the active compound with finely divided solid substances, for example talc or natural clays, such as kaolin, bentonite, pyrophillite or diatomaceous earth. Granules can be prepared either by atomizing the active compound onto an absorbent, granular inert material, or applying active compound concentrates to the surface of carriers, such as sand or kaolinites, or of a granular inert material, by means of adhesives, for example polyvinyl alcohol, sodium polyacrylate or mineral oils. Suitable active compounds can also be formulated in the manner customary for the preparation of fertilizer granules—if desired as mixtures with fertilizers.

The active compound concentration in wettable powders varies, for example, between about 10% and 80%, the remainder consisting of the abovementioned formulation additives. The active compound concentration in emulsifiable concentrates can likewise be about 10% to 80%. Dust-like formulations contain at most 5–20% of active compound, and solutions which can be sprayed contain about 2–20%. In the case of granules, the active ingredient content partly depends on whether the active compound is liquid or solid, and which granulation auxiliaries, fillers and the like are used.

For use, the commercially available concentrates are diluted, if appropriate, in the customary manner, for example by means of water in the case of wettable powders and emulsifiable concentrates. The ready-to-spray suspensions preferably contain 0.05 to 2%, in particular 0.1 to 1%, of active compound. Dust-like and granular formulations, and solutions which can be sprayed are not diluted more with further inert substances before use.

PREPARATION EXAMPLES

Example 1

O,O-Diethyl O-(2-ethoxy-3-carbethoxy-4-quinolinyl) thiophosphate

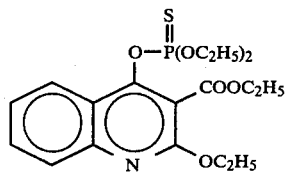

5.6 g (0.05 mol) of potassium tert.-butylate are suspended in 150 ml of absolute acetonitrile, and 13 g (0.05 mol) of 2-ethoxy-3-carbethoxy-4-hydroxyquinoline are added. The mixture is stirred at 50° C. for about 30 minutes. After 9.4 g (0.05 mol) of O,O-diethylthiophosphoryl chloride have been added, the reaction mixture is stirred at 50°–60° C. for 5 hours and is then concentrated in vacuo. The residue is taken up in 200 ml cf toluene and the mixture is extracted by stirring successively with 100 ml of water, 100 ml of 1 N sodium hydroxide solution and another 100 ml of water. The organic phase is dried with sodium sulfate. After the solvent has been distilled off in vacuo, 17.2 g of O,O-diethyl-O-(2-ethoxy-3-carbethoxy-4-quinolyl) thiophosphate with a refractive index of $n_D^{23}$ of 1.5452 are obtained.

The following compounds are obtained in an analogous manner:

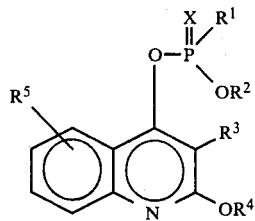

FORMULATION EXAMPLES

Example a

An emulsifiable concentrate is obtained from 15 parts by weight of active compound, 75 parts by weight of cyclohexanone, as the solvent, and 10 parts by weight of oxyethylated nonyl phenol (oxyethylated with 10 mols of ethylene oxide), as the emulsifier.

Example b

A wettable powder which is readily dispersible in water is obtained by mixing 25 parts by weight of active compound, 64 parts by weight of activated salicic acid,

TABLE

| Example No. | $R^1$ | $R^2$ | $R^3$ | $R^4$ | $R^5$ | X | Physical data |
|---|---|---|---|---|---|---|---|
| 2 | $OC_2H_5$ | $C_2H_5$ | $COOC_2H_5$ | $C_2H_5$ | H | O | $n_D^{31.5}$: 1.5252 |
| 3 | S—n-$C_3H_7$ | $C_2H_5$ | $COOC_2H_5$ | $C_2H_5$ | H | O | $n_D^{22}$: 1.5459 |
| 4 | S—n-$C_3H_7$ | $C_2H_5$ | $COOC_2H_5$ | $C_2H_5$ | H | S | $n_D^{23}$: 1.5723 |
| 5 | $CH_3$ | $C_2H_5$ | $COOC_2H_5$ | $C_2H_5$ | H | S | $n_D^{28}$: 1.5622 |
| 6 | $C_2H_5$ | $CH_3$ | $COOC_2H_5$ | $C_2H_5$ | H | S | melting point: 63–67% |
| 7 | $C_2H_5$ | $C_2H_5$ | $COOC_2H_5$ | $C_2H_5$ | H | S | $n_D^{31.5}$: 1.5533 |
| 8 | $C_2H_5$ | i-$C_3H_7$ | $COOC_2H_5$ | $C_2H_5$ | H | S | $n_D^{27.5}$: 1.5503 |
| 9 | S—n-$C_3H_7$ | $C_2H_5$ | $COOCH_3$ | $C_2H_5$ | H | O | $n_D^{21}$: 1.5532 |
| 10 | S—n-$C_3H_7$ | $C_2H_5$ | $COOCH_3$ | $C_2H_5$ | H | S | $n_D^{20}$: 1.5747 |
| 11 | S—n-$C_3H_7$ | $C_2H_5$ | COO—n-$C_3H_7$ | $C_2H_5$ | H | O | |
| 12 | S—n-$C_3H_7$ | $C_2H_5$ | COO—n-$C_3H_7$ | $C_2H_5$ | H | S | |
| 13 | S—n-$C_3H_7$ | $C_2H_5$ | COO—i-$C_3H_7$ | $C_2H_5$ | H | O | $n_D^{21}$: 1.5445 |
| 14 | S—n-$C_3H_7$ | $C_2H_5$ | COO—i-$C_3H_7$ | $C_2H_5$ | H | S | $n_D^{25}$: 1.5648 |
| 15 | S—n-$C_3H_7$ | $C_2H_5$ | $COOC_2H_5$ | $CH_3$ | H | O | $n_D^{21}$: 1.5588 |
| 16 | S—n-$C_3H_7$ | $C_2H_5$ | $COOC_2H_5$ | $CH_3$ | H | S | $n_D^{24}$: 1.5808 |
| 17 | S—n-$C_3H_7$ | $C_2H_5$ | $COOC_2H_5$ | n-$C_3H_7$ | H | O | $n_D^{21}$: 1.5452 |
| 18 | S—n-$C_3H_7$ | $C_2H_5$ | $COOC_2H_5$ | n-$C_3H_7$ | H | S | $n_D^{23}$: 1.5649 |
| 19 | S—n-$C_3H_7$ | $C_2H_5$ | $COOC_2H_5$ | i-$C_3H_7$ | H | O | |
| 20 | S—n-$C_3H_7$ | $C_2H_5$ | $COOC_2H_5$ | i-$C_3H_7$ | H | S | |
| 21 | S—n-$C_3H_7$ | $C_2H_5$ | CONH—$C_3H_7$ | $C_2H_5$ | H | O | |
| 22 | S—n-$C_3H_7$ | $C_2H_5$ | CONH—$C_3H_7$ | $C_2H_5$ | H | S | |
| 23 | S—n-$C_3H_7$ | $C_2H_5$ | CONH—i-$C_3H_7$ | $C_2H_5$ | H | O | |
| 24 | S—n-$C_3H_7$ | $C_2H_5$ | CONH—i-$C_3H_7$ | $C_2H_5$ | H | S | Oil |
| 25 | S—$C_2H_5$ | $C_2H_5$ | $COON(CH_3)_2$ | $C_2H_5$ | H | O | |
| 26 | S—n-$C_3H_7$ | $C_2H_5$ | $COON(CH_3)_2$ | $C_2H_5$ | H | S | |
| 27 | S—$CH_3$ | $C_2H_5$ | $COON(C_2H_5)_2$ | $C_2H_5$ | H | O | |
| 28 | S—n-$C_3H_7$ | $C_2H_5$ | $COON(C_2H_5)_2$ | $C_2H_5$ | H | S | |
| 29 | S—n-$C_3H_7$ | $C_2H_5$ | CN | $C_2H_5$ | H | O | $n_D^{20}$: 1.5732 |
| 30 | S—n-$C_3H_7$ | $C_2H_5$ | CN | $C_2H_5$ | H | S | $n_D^{23}$: 1.5879 |
| 31 | S—n-$C_3H_7$ | $C_2H_5$ | Cl | $C_2H_5$ | H | O | |
| 32 | S—n-$C_3H_7$ | $C_2H_5$ | Cl | $C_2H_5$ | H | S | |
| 33 | $OC_2H_5$ | $C_2H_5$ | H | $C_2H_5$ | H | S | $n_D^{31.5}$: 1.5529 |
| 34 | S—n-$C_3H_7$ | $C_2H_5$ | H | $C_2H_5$ | H | O | $n_D^{19}$: 1.5647 |
| 35 | S—n-$C_3H_7$ | $C_2H_5$ | H | $C_2H_5$ | H | S | $n_D^{23}$: 1.5855 |
| 36 | $C_2H_5$ | $C_2H_5$ | H | $C_2H_5$ | H | S | $n_D^{31.5}$: 1.5626 |
| 37 | NH—i-$C_3H_7$ | $C_2H_5$ | H | $C_2H_5$ | H | S | melting point: 55–58° C. |
| 38 | S—n-$C_3H_7$ | $C_2H_5$ | $COOC_2H_5$ | $C_2H_5$ | 8-Cl | O | $n_D^{21}$: 1.5623 |
| 39 | S—n-$C_3H_7$ | $C_2H_5$ | $COOC_2H_5$ | $C_2H_5$ | 7-Cl | O | $n_D^{20}$: 1.5598 |
| 40 | S—n-$C_3H_7$ | $C_2H_5$ | $COOC_2H_5$ | $C_2H_5$ | 7-Cl | S | $n_D^{20}$: 1.5765 |
| 41 | S—n-$C_3H_7$ | $C_2H_5$ | $COOC_2H_5$ | $C_2H_5$ | 6-Cl | O | melting point: 49–50° C. |
| 42 | S—n-$C_3H_7$ | $C_2H_5$ | $COOC_2H_5$ | $C_2H_5$ | 6-Cl | S | $n_D^{20}$: 1.5743 |
| 43 | S—n-$C_3H_7$ | $C_2H_5$ | $COOC_2H_5$ | $C_2H_5$ | 5-Cl | O | $n_D^{20}$: 1.5627 |
| 44 | S—n-$C_3H_7$ | $C_2H_5$ | $COOC_2H_5$ | $C_2H_5$ | 5-Cl | S | $n_D^{20}$: 1.5763 |
| 45 | S—n-$C_3H_7$ | $C_2H_5$ | $COOC_2H_5$ | $C_2H_5$ | 7-Br | O | $n_D^{20}$: 1.5662 |
| 46 | S—n-$C_3H_7$ | $C_2H_5$ | $COOC_2H_5$ | $C_2H_5$ | 7-Br | S | $n_D^{20}$: 1.5852 |
| 47 | S—n-$C_3H_7$ | $C_2H_5$ | $COOC_2H_5$ | $C_2H_5$ | 6-Br | O | $n_D^{21}$: 1.5712 |
| 48 | S—n-$C_3H_7$ | $C_2H_5$ | $COOC_2H_5$ | $C_2H_5$ | 6-Br | S | $n_D^{20}$: 1.5862 |
| 49 | S—n-$C_3H_7$ | $C_2H_5$ | $COOC_2H_5$ | $C_2H_5$ | 7-$NO_2$ | O | melting point: 59–68° C. |
| 50 | S—n-$C_3H_7$ | $C_2H_5$ | $COOC_2H_5$ | $C_2H_5$ | 7-$CH_3$ | O | |
| 51 | S—n-$C_3H_7$ | $C_2H_5$ | $COOC_2H_5$ | $C_2H_5$ | 7-$CH_3$ | S | |
| 52 | S—n-$C_3H_7$ | $C_2H_5$ | $COOC_2H_5$ | $C_2H_5$ | 6-$CH_3$ | O | $n_D^{20}$: 1.5513 |
| 53 | S—n-$C_3H_7$ | $C_2H_5$ | $COOC_2H_5$ | $C_2H_5$ | 6-$CH_3$ | S | $n_D^{20}$: 1.5688 |
| 54 | S—n-$C_3H_7$ | $C_2H_5$ | $COOC_2H_5$ | $C_2H_5$ | 7-$OCH_3$ | O | |
| 55 | S—n-$C_3H_7$ | $C_2H_5$ | $COOC_2H_5$ | $C_2H_5$ | 7-$OCH_3$ | S | |
| 56 | S—n-$C_3H_7$ | $C_2H_5$ | $COOC_2H_5$ | $C_2H_5$ | 7-$CF_3$ | O | $n_D^{21}$: 1.5183 |
| 57 | Phenyl | $C_2H_5$ | $COOC_2H_5$ | $C_2H_5$ | H | O | |
| 58 | Phenyl | $C_2H_5$ | $COOC_2H_5$ | $C_2H_5$ | H | S | | as the inert substance, and 10 parts by weight of calcium lignin-sulfonate and 1 part by weight of sodium oleyl-methyl-taurate, as the wetting agent and dispersing agent, and grinding the mixture in a pinned disc mill.

Example c

A dusting agent is obtained by mixing 10 parts by weight of active compound and 90 parts by weight of talc, as the inert substance, and comminuting the mixture in an impact mill.

Example d

Granules consist, for example, of about 2–15 parts by weight of active compound and 98–85 parts by weight of inert granular materials, such as, for example, attapulgite, pumice and quartz sand.

BIOLOGICAL EXAMPLES

Example I

Field beans (*Vicia faba*) heavily infested with courpea aphid (*Aphis craccivora*) were sprayed with an aqueous suspension of a wettable powder concentrate containing 0.0125% by weight of the active compound from Example 3, until the suspension drips off. The plants were placed in a greenhouse, and 100% destruction of the test animals was detected 3 days after the treatment. The compounds according to Examples 4, 33 and 35 proved to be equally effective.

Example II

Bean plants (*Phaseolus vulgaris*) heavily infested with two-spotted spider mites (*Tetranychus urticae* normal-sensitive) were sprayed with an aqueous solution of a wettable powder concentrate containing 0.0125% by weight of the active compound from Example 3, until the suspension starts to drip off. A microscopic check 8 days after the treatment showed that all the stages of the population had been killed. When tested in the same manner, the compounds according to Examples 4, 33, 34, 35, 36 and 37 proved to be equally effective.

Example III

Red cotton bugs (*Oncopeltus fasciatus*) were sprayed with aqueous dilutions of wettable powder concentrates (in each case 0.025% by weight of active compound in the spray liquor) of the active compounds from Examples 1, 33, 36 and 37 until dripping wet. The bugs were then placed in containers with lids which were permeable to air. The mortality was evaluated 5 days after the treatment, and was 100% in each individual case.

Example IV 1 ml of the compound to be tested (Example 3) was uniformly applied, as the active compound in acetone with a concentration of 0.0125% by weight, to the inside of the lid and of the bottom of a Petri dish by means of a pipette, and the dish was left open until all of the solvent had evaporated. 10 houseflies (*Musca domestica*) were then placed into each Petri dish, the dishes were closed with the lids, and 100% destruction of the test animals was found after 3 hours.

The compounds according to Examples 36 and 37 proved to be equally effective.

Example V

As described in Example IV, the compound from Example 3 was uniformly applied, as the active compound in acetone with a concentration of 0.025% by weight, to the inside of the lid and of the bottom of a Petri dish, and the solution was allowed to dry. 10 larvae (L 4) of the German cockroach (*Blatella germanica*) were then placed in each Petri dish, the dishes were closed with the lids, and 100% destruction of the test animals was found after 72 hours.

The compound according to Example 36 proved to be equally effective.

Example VI

Cotton leaves (Gossypium sp.) were sprayed ($\triangleq$ 600 l of spray liquor/ha) with an aqueous emulsion of the compound according to Example 3 in an active compound concentration of 0.025% by weight, and caterpillars (10 specimens, L 3–4 stage) of the cotton worm (*Prodenia litura*) which had been likewise treated were placed on the cotton leaves. The leaves and caterpillars were together placed in observation cages, and 100% destruction of the test animals was found after 48 hours. The compounds according to Examples 34, 35 and 4 proved to be equally effective.

Example VII

Cabbage leaves (*Brassica oleracea*) were sprayed, as described in Example VI, with an aqueous emulsion of the compound according to Example 3 in a concentration of 0.0125% by weight, and caterpillars (10 specimens, 3–4 stage) of the diamond-back moth (*Plutella xylostella*) which had been likewise treated were placed on the leaves.

The leaves and caterpillars were together placed in observation cages, and 100% destruction of the test animals was found after 48 hours.

Example VIII

Cabbage leaves were treated, as in Example VII, with the compound from Example 3 and caterpillars (10 specimens, L 3–4) of the cabbage moth (*Mamestra brassicae*) which had been likewise treated were placed on the leaves, and the leaves and caterpillars were together placed in observation cages. 100% destruction of the test animals was found after 48 hours.

Example IX

Bean leaves (*Phaseolus vulgaris*) were treated with an aqueous emulsion of the compound from Example 3 in a concentration of 0.0125% by weight (relative to the active compound) and were placed in observation cages with larvae of the Mexican bean weevil (*Epilachna varivestis*) which had been treated in the same way. Evaluation after 48 hours showed 100% destruction of the test animals.

The compounds according to Examples 4 and 35 proved to be equally effective.

Example X

Rice plants in the 4-leaf stage were sprayed until dripping wet with the compounds given in Table I in concentrations of 1000, 500, 250 and 125 mg of active compound/liter of spray liquor. After the spray coating had dried on, the plants were uniformly sprayed with a spore suspension of *Piricularia oryzae* and were placed in a climatically controlled chamber at 25° C. and 100% relative atmospheric humidity for 48 hours. The plants were then kept in a greenhouse at 25° C. and 85% relative atmospheric humidity, and, 14 days after the inoculation, were investigated for *Piricularia oryzae* infection.

The degree of infection was expressed in % of infected leaf area, relative to the untreated, infected control plants (=100% infection).

TABLE I

| Compound according to Example | Area of leaf infected with *Piricularia oryzae* in %, at | | | |
|---|---|---|---|---|
| | 1000 | 500 | 250 | 125 |
| | mg of active compound/liter of spray liquor | | | |
| 2 | 0 | 0 | 0–3 | 3 |
| 3 | 0 | 0 | 0 | 0 |
| Untreated infected plants | | 100 | | |

The excellent fungicidal action of the compounds claimed against *Piricularia oryzae* can be seen from Example X.

Example XI

Wheat plants were treated with the compounds claimed in Table II in use concentrations of 1000, 500, 250 and 125 mg of active compound/liter of spray liquor. After the coating of active compound had dried on, the plants were inoculated with spores of brown rust of wheat and were placed, dripping wet, in a climatically controlled chamber at 20° C. and 100% relative atmospheric humidity. 24 hours later, the plants were returned to a greenhouse and, 14 days after the inoculation, were investigated for brown rust of wheat infection. The degree of infection was expressed in % of infected leaf area, relative to the untreated, infected control plants (=100% infection). Table II shows the good action of the compounds investigated.

TABLE II

| Compound according to Example | % leaf area infected with brown rust at | | | |
|---|---|---|---|---|
| | 1000 | 500 | 250 | 125 |
| | mg of active compound/liter of spray liquor | | | |
| 3 | 0 | 0 | 0 | 0 |
| 37 | 0 | 0 | 0–3 | 3 |
| 36 | 0 | 0 | 0–3 | 3 |
| 2 | 0 | 0 | 0 | 0 |
| 34 | 0 | 0 | 0–3 | 0 |
| Untreated infected plants | | 100 | | |

Example XII

The compound claimed was uniformly mixed and distributed into soil which had been uniformly and heavily contaminated with *Pythium ultimum*. The soil thus treated was filled into plastic posts, and 10 pea seeds were then sown into each pot. 8–10 days after sowing, the tests were evaluated by determining the number of emerged, healthy plants and calculating the degree of action of the compound claimed. Pots containing infected, untreated soil served as controls.

TABLE III

| Compound according to Example | Degree of action in % for | | | |
|---|---|---|---|---|
| | 200 | 100 | 50 | 25 |
| | mg of active compound/kg of soil | | | |
| 34 | 100 | 100 | 100 | 70 |
| Untreated infected soil | | 0 | | |

We claim:

1. A compound of the formula I

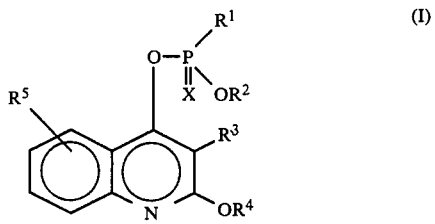

in which $R^1$ denotes $(C_1-C_4)$-alkyl, $(C_1-C_4)$-alkoxy, $(C_1-C_4)$-alkylmercapto, $(C_1-C_4)$-alkylamino, $(C_1-C_4)$-dialkylamino or phenyl, $R^2$ denotes $(C_1-C_4)$-alkyl, $R^3$ denotes hydrogen, halogen, COOalkyl, CONH(alkyl) or CON(alkyl)$_2$ with in each case 1–4 C atoms per alkyl radical, or cyano, $R^4$ denotes $(C_1-C_4)$-alkyl, $R^5$ denotes hydrogen, halogen, nitro, $(C_1-C_4)$-alkyl, $(C_1-C_4)$-alkoxy or trihalogenomethyl and X denotes oxygen or sulfur.

2. O-ethyl-O-(2-ethoxy-3-carbethoxy-4-quinolinyl) S-n-propyl thiophosphate.

3. An insecticidal, acaricidal or fungicidal composition containing an insecticidally, acaricidally or fungicidally effective amount of a compound defined in claim 1 and a customary formulation auxiliary.

4. An insecticidal, acaricidal or fungicidal composition containing an insecticidally, acaricidally or fungicidally effective amount of the compound of claim 2 and a customary formulation auxiliary.

5. A method for combatting insects, acarids or fungi which comprises contacting insects, acarids or fungi with an insecticidally, acaricidally or fungicidally effective amount of a compound defined in claim 1.

6. A method for combatting insects, acarids or fungi which comprises contacting insects, acarids or fungi with an insecticidally, acaricidally or fungicidally effective amount of the compound of claim 2.

* * * * *